United States Patent
Waner et al.

[11] Patent Number: 5,643,252
[45] Date of Patent: Jul. 1, 1997

[54] LASER PERFORATOR

[75] Inventors: Milton Waner; Stephen T. Flock, both of Little Rock; Charles H. Vestal, Sheridan, all of Ark.

[73] Assignee: Venisect, Inc., Little Rock, Ark.

[21] Appl. No.: 126,241

[22] Filed: Sep. 24, 1993

Related U.S. Application Data

[63] Continuation-in-part of Ser. No. 968,862, Oct. 28, 1992, abandoned.

[51] Int. Cl.$^6$ .................................................. A61B 17/36
[52] U.S. Cl. ................. 606/9; 606/3; 606/10; 606/17; 607/89; 604/21; 128/770
[58] Field of Search ............. 606/2–7, 9–19, 606/27–29; 607/88, 89; 604/21, 22; 128/770

[56] References Cited

U.S. PATENT DOCUMENTS

| | | | |
|---|---|---|---|
| 3,865,113 | 2/1975 | Sharon et al. | 606/18 |
| 4,648,892 | 3/1987 | Kittrell et al. | 606/15 |
| 4,775,361 | 10/1988 | Jacques et al. . | |
| 4,940,411 | 7/1990 | Vassiliadis et al. | 606/16 |
| 4,941,093 | 7/1990 | Marshall et al. | 606/5 |
| 5,066,293 | 11/1991 | Furumoto | 606/9 |
| 5,125,922 | 6/1992 | Dwyer et al. | 606/10 |
| 5,165,418 | 11/1992 | Tankovich . | |
| 5,342,355 | 8/1994 | Long | 606/29 |
| 5,360,426 | 11/1994 | Muller et al. | 606/13 |
| 5,397,327 | 3/1995 | Koop et al. | 606/17 |
| 5,423,798 | 6/1995 | Crow | 606/10 |
| 5,437,658 | 8/1995 | Muller et al. | 606/17 |
| 5,461,212 | 10/1995 | Seiler et al. | 606/17 |

FOREIGN PATENT DOCUMENTS

| | | |
|---|---|---|
| 4-314428 | 11/1992 | Japan . |
| 7-39542 | 2/1995 | Japan . |
| 1614808 | 3/1988 | U.S.S.R. . |
| 1670858 | 10/1989 | U.S.S.R. . |
| 2005515 | 1/1994 | U.S.S.R. . |
| 2027450 | 1/1995 | U.S.S.R. . |

OTHER PUBLICATIONS

"Laser Scarifier" advertisement in Russian, published Nov. 19, 1990; translation into English provided.

*Primary Examiner*—Angela D. Sykes
*Assistant Examiner*—Michael Peffley
*Attorney, Agent, or Firm*—Lyon & Lyon LLP

[57] ABSTRACT

This invention provides a device and method for perforation of skin for the purpose of drawing blood or administering pharmaceuticals. The device incorporates a laser which produces a laser beam at an appropriate wavelength which is specifically focused to perforate the skin of a patient. Optionally a container can be incorporated in the device for collecion of blood from the perforated tissue.

50 Claims, 5 Drawing Sheets

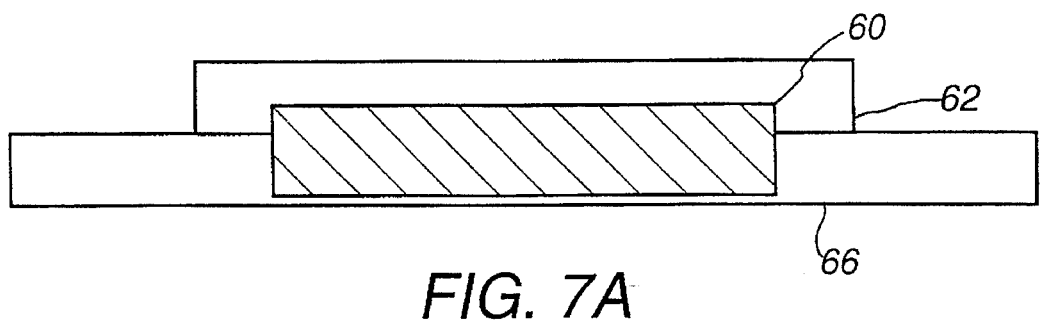
FIG. 7A
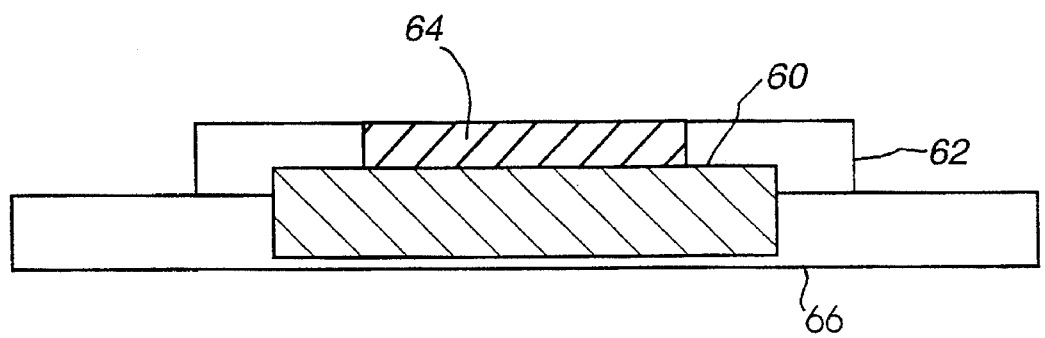
FIG. 7B
FIG. 8
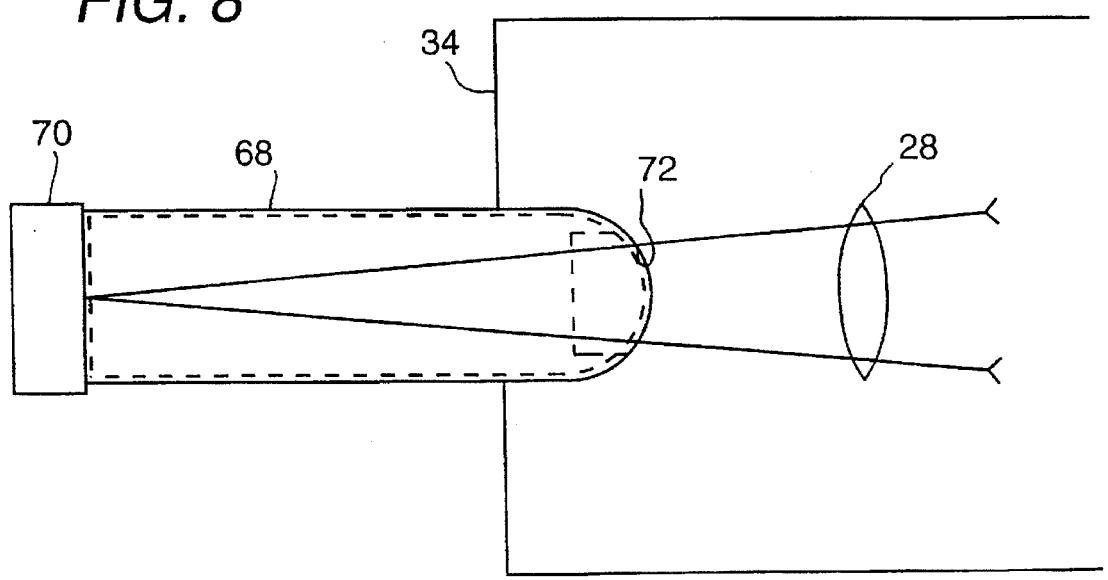

LASER PERFORATOR

This application is a continuation-in-part of U.S. Ser. No. 07/968,862, filed Oct. 28, 1992 (now abandoned).

FIELD OF THE INVENTION

This invention is in the field of medical equipment, namely laser medical equipment.

BACKGROUND

The traditional method for the collection of small quantities of blood from a patient utilizes mechanical perforation of the skin with a sharp device such as a metal lancet or needle. This procedure has many drawbacks, two of which are the possible infection of health-care workers or the public at large with the device used to perforate the skin, and the costly handling and disposal of biologically hazardous waste.

When skin is perforated with a sharp device such as a metal lancet or needle, biological waste is created in the form of the "sharp" which is contaminated by the patient's blood and/or tissue. If the patient is infected with any number of blood-born agents, such as human immunodeficiency virus (HIV) which causes autoimmune deficiency syndrome (AIDS), hepatitis virus, or the etiological agent of other diseases, the contaminated sharp can pose a serious threat to others who might come in contact with it. There are many documented instances of HIV infection of medical workers who were accidentally stabbed by a contaminated sharp.

Disposal of sharps is also a major problem. Disposal of contaminated materials poses both a logistics and a financial burden on the end user such as the medical institution. In the 1980s, numerous instances of improperly disposed biological wastes being washed up on public beaches have occurred. The potential for others, such as intravenous drug users, to obtain improperly disposed needles is also problematic.

There exists an additional drawback of the traditional method of being stabbed by a sharp instrument for the purpose of drawing blood. Often, the stabbing procedure must be repeated before sufficient blood is obtained. This can cause significant stress and anxiety in the patient.

Clearly the current procedure for puncturing skin for the purpose of drawing blood has significant inherent problems. These problems arise because a sharp instrument is used in the procedure. Thus, a need exists for a technique to puncture skin which does not use a sharp instrument. This method would obviate the need for disposal of contaminated instruments, and reduce the risk of cross infection.

Lasers have been used in recent years as a very efficient precise tool in a variety of surgical procedures. Among potentially new sources of laser radiation, the rare-earth elements are of major interest for medicine. The most promising of these is a YAG (yttrium, aluminum, garnet) crystal doped with erbium (Er) ions. With the use of this crystal, it is possible to build an erbium-YAG (Er:YAG) laser which can be configured to emit electromagnetic energy at a wavelength (2.94 microns) which is strongly absorbed by water. When tissue, which consists mostly of water, is irradiated with radiation at or near this wavelength, it is rapidly heated. If the intensity of the radiation is sufficient, the heating is rapid enough to cause the vaporization of tissue. Some medical uses of Er:YAG lasers have been described in the health-care disciplines of dentistry, gynecology and ophthalmology. See, e.g., Bogdasarov, B. V., et al., "The Effect of YAG:Er Laser Radiation on Solid and Soft Tissues," Preprint 266, Institute of General Physics, Moscow, 1987; Bol'shakov, E. N. et al., "Experimental Grounds for YAG:Er Laser Application to Dentistry," SPIE 1353:160–169, Lasers and Medicine (1989).

SUMMARY OF THE INVENTION

This invention utilizes a laser beam to perforate the skin of a patient. The perforation is produced by irradiating the surface of the skin by a focused pulse of electromagnetic energy emitted by a laser. It is possible to very precisely perforate skin to a selectable depth without causing clinically relevant damage to healthy proximal tissue by a judicious selection of the following irradiation parameters: wavelength, energy fluence (determined by dividing the energy of the pulse by the area irradiated), pulse temporal width and irradiation spot size.

A device is provided which emits a pulsed laser beam, focused to a small spot for the purpose of perforating tissue. By adjusting the output of the laser, the depth, width and length of the perforation can be controlled to fit the purpose for which the perforation is required. This method can be used to create a small, relatively shallow hole in the skin which penetrates into the capillary bed, thus allowing the drawing of blood for a variety of purposes. Optionally a tissue pre-heating device can be added to increase blood flow prior to the laser perforation. Safety interlocks are advantageously incorporated in the device to prevent hazardous operation and accidental laser-irradiations.

This device can further be modified to include a container. Such a container can be added to: (1) increase the efficiency in the collection of blood and serum; (2) reduce the noise created when the laser beam perforates the patient's tissue; and (3) collect the ablated tissue. The container is optionally evacuated to expedite the collection of blood and serum. In one embodiment, the container collects only ablated tissue. The noise created from the laser beam's interaction with the patient's skin may cause the patient anxiety. The optional container reduces the noise intensity and therefore alleviates the patient's anxiety and stress. The container also minimizes the risk of cross-contamination and guarantees the sterility of the collected sample. The placement of the container in the device of this invention is unique in that it covers the tissue being punctured, at the time of puncture by the laser beam, and is therefore able to collect the blood sample and/or ablated tissue as the puncturing occurs.

This invention also provides a means for puncturing the skin of a patient in a manner that does not result in bleeding. The perforation created typically penetrates through the keratin layer or both the keratin layer and the epidermis. This will allow the administration of pharmaceuticals through the skin. There are several advantages to administering drugs in this fashion, for example: drugs can be administered continually on an out-patient basis over long periods of time, and the speed and/or efficiency of drug delivery can be enhanced for drugs which were either slow or unable to penetrate skin. Furthermore, this method of delivery provides an alternative delivery route for drugs that would otherwise require to be injected.

This invention avoids the use of sharps. The absence of a contaminated sharp will eliminate the risk of accidental injury and its attendant risks to the healthcare worker, the patient, and anyone who may come into contact with the sharp, whether by accident or by necessity.

The absence of sharps also obviates the need for disposal of biologically hazardous waste. Thus, this invention provides an ecologically sound method of perforating skin.

The device of this invention requires no special skills to use. It is small, light-weight and can be used with rechargeable batteries. This portability and ease of use makes possible the utility of the device in a variety of settings, such as a hospital room, clinic, or home.

The safety features incorporated into this device do not require that any special safety eyewear be worn by the operator of the device, the patient, or anyone else in the vicinity of the device when it is being used. This is a marked improvement over prior art laser devices which require such special protection.

BRIEF DESCRIPTION OF THE DRAWINGS

The present invention may be better understood and its advantages appreciated by those skilled in the art by referring to the accompanying drawings wherein

FIG. 7 shows alternative patches for sterilization and/or delivery of pharmaceutical.

FIG. 8 shows an optional container for collecting blood and ablated tissue, and for reducing noise resulting from the interaction between the laser and the patient's tissue.

DETAILED DESCRIPTION OF THE PREFERRED EMBODIMENTS

Figure 1:
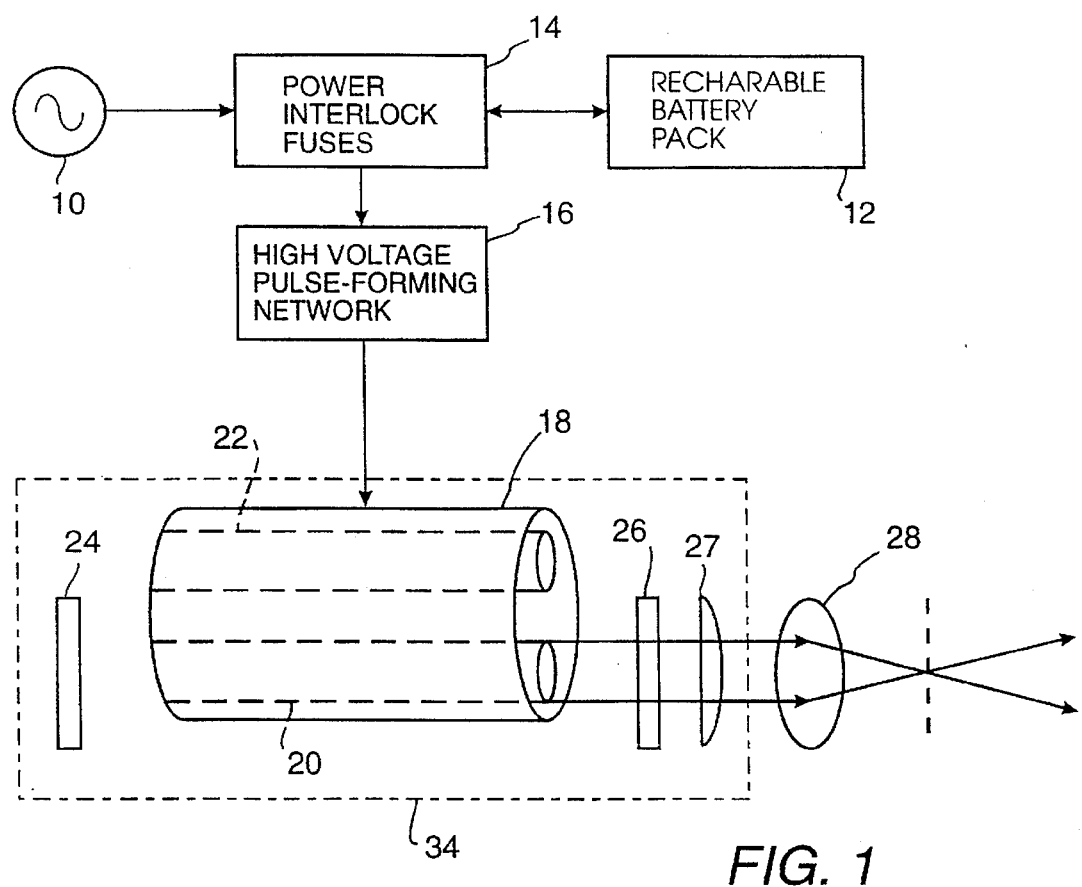
FIG. 1 shows the laser device with its power source, high voltage pulse-forming network, flashlamp, lasing rod, mirrors, housing and focusing lens.

This invention provides a method and device for perforating skin for either the sampling of blood or the administration of pharmaceuticals. The device utilizes a laser beam, specifically focused, and lasing at an appropriate wavelength, preferably between 2 and 7 microns, to create small holes in the skin of a patient. The laser beam is focused with a lens to produce an irradiated spot on the skin with a size of approximately 0.1–1 mm diameter, and an energy fluence in the range of 10–100,000 J/cm$^2$. Optionally, the spot can be slit-shaped, with a width of 0.05–0.5 mm and a length of up to 2.5 mm.

The Device

As shown in the Figures, the device comprises a power connection which can be either a standard electrical supply 10, or optionally a rechargeable battery pack 12, optionally with a power interlock switch 14 for safety purposes; a high voltage pulse-forming network 16; a laser pump-cavity 18 containing a laser rod 20, preferably Er:YAG; a means for exciting the laser rod, preferably a flashlamp 22 supported within the laser pump-cavity; an optical resonator comprised of a high reflectance mirror 24 positioned posterior to the laser rod and an output coupling mirror 26 positioned anterior to the laser rod; a transmitting focussing lens 28 positioned beyond the output coupling mirror; optionally a second focusing cylindrical lens 27 positioned between the output coupling mirror and the transmitting focusing lens; an applicator 30 for positioning the subject skin at the focal point of the laser beam, which is optionally heated for example with a thermoelectric heater 32, attached to the laser housing 34; an interlock 36 positioned between the applicator and the power supply; and optionally a beam dump 38 attached to the applicator with a fingertip access port 40.

Figure 2:
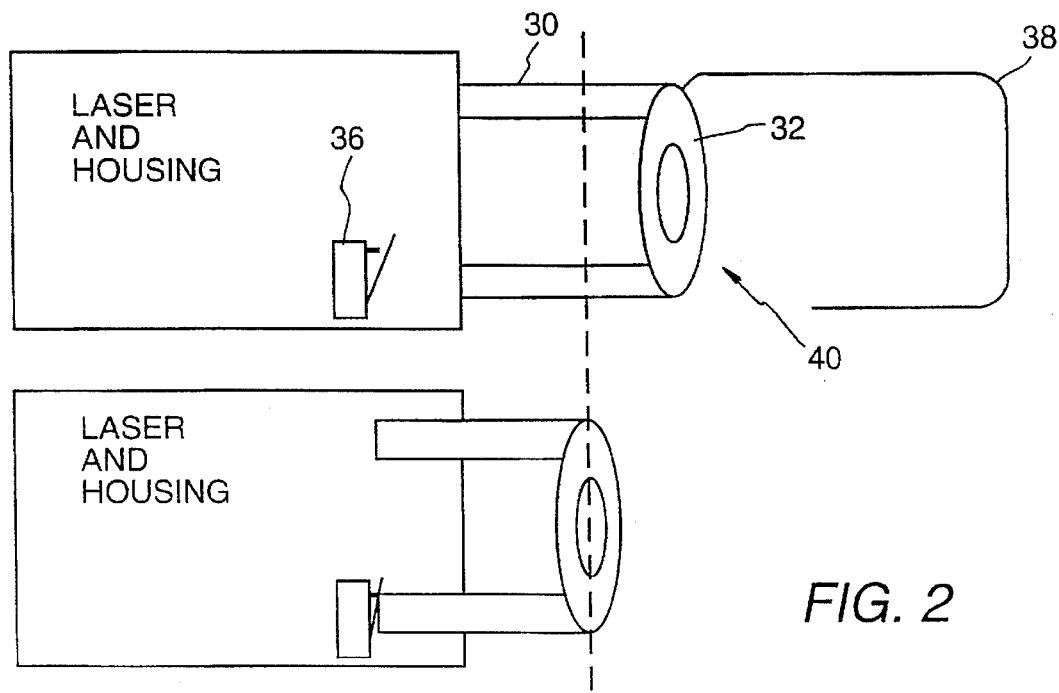
FIG. 2 shows an optional spring-loaded interlock and optionally heated applicator.

FIGS. 1–2 are diagrammatic representations of the preferred embodiment of the device of the invention. The device preferably draws power from a standard 110 V or 220 V line 10 (single phase, 50 or 60 Hz) which is rectified and used to charge up a bank of capacitors included in the high voltage pulse-forming network 16. Optionally, a rechargeable battery pack 12 can be used instead. The bank of capacitors establishes a high DC voltage across a high-output flashlamp 22. Optionally a power interlock 14, such as a keyswitch, can be provided which will prevent accidental charging of the capacitors and thus accidental laser excitation. A further interlock can be added to the device at the applicator, such as a spring-loaded interlock 36, so that discharge of the capacitors requires both interlocks to be enabled.

With the depression of a switch, a voltage pulse can be superimposed on the already existing voltage across the flashlamp in order to cause the flashlamp to conduct, and, as a consequence, initiate the flash. The light from the flashlamp is located in the laser cavity 18 that has a shape such that most of the light is efficiently directed to the laser rod 20, which absorbs the light, and, upon de-excitation, subsequently lases. The laser cavity mirrors of low 26 and high 24 reflectivity, positioned collinearly with the long-axis of the laser rod, serve to amplify and align the laser beam.

Figure 3:
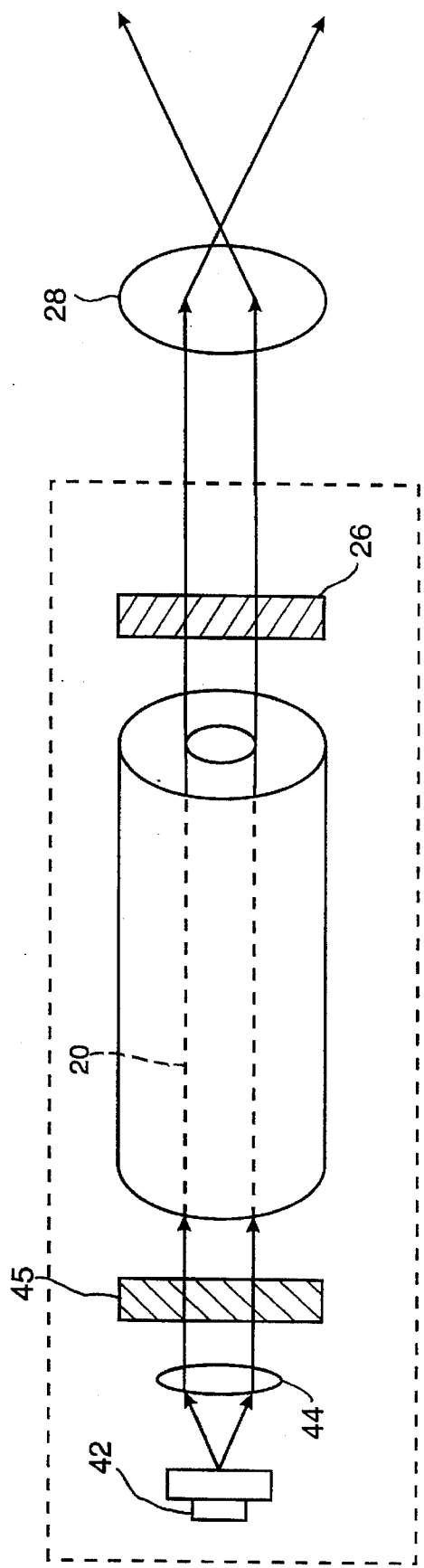
FIG. 3 shows an alternative means of exciting the laser rod using a diode laser.

Optionally, as shown in FIG. 3, a diode laser 42 which produces a pump-beam collinear with the long-axis of the laser crystal can be used instead of the flashlamp to excite the crystal. The pump-beam of this laser is collimated with a collimating lens 44, and transmitted to the primary laser rod through the high reflectance infrared mirror 45. This high reflectance mirror allows the diode pump laser beam to be transmitted, while reflecting infrared light from the primary laser.

The Er:YAG lasing material is the preferred material for the laser rod because the wavelength of the electromagnetic energy emitted by this laser, 2.94 microns, is very near one of the peak absorption wavelengths (approximately 3 microns) of water. Thus, this wavelength is strongly absorbed by water. The rapid heating of water causes perforation of the skin.

Other useful lasing material is any material which, when induced to lase, emits a wavelength that is strongly absorbed by tissue, such as through absorption by water or nucleic acids or proteins, and consequently causes the required perforation of the skin. A laser can effectively cut tissue to create the desired perforations where tissue exhibits an absorption coefficient of 10–10,000 cm$^{-1}$. Examples of useful lasing elements are pulsed $CO_2$ lasers, Ho:YAG (holmium:YAG), Er:YAP, Er/Cr:YSGG (erbium/chromium: yttrium, scandium, gallium, garnet; 2.796 microns), Ho:YSGG (holmium:YSGG; 2.088 microns), Er:GGSG (erbium:gadolinium, gallium, scandium, garnet), Er:YLF (erbium:yttrium, lithium, fluoride; 2.8 microns), Tm:YAG (thulium:YAG; 2.01 microns), Ho:YAG (holmium:YAG; 2.127 microns); Ho/Nd:YAlO$_3$ (holmium/neodymium:yttrium, aluminate; 2.85–2.92 microns), cobalt:MgF$_2$ (cobalt: magnesium fluoride; 1.75–2.5 microns), HF chemical (hydrogen fluoride; 2.6–3 microns), DF chemical (deuterium fluoride; 3.6–4 microns), carbon monoxide (5–6 microns), deep UV lasers, and frequency tripled Nd:YAG (neodymium:YAG, where the laser beam is passed through crystals which cause the frequency to be tripled).

Utilizing current technology, some of these laser materials provide the added benefit of small size, allowing the laser perforator device to be small and portable. In addition to Er:YAG, Ho:YAG lasers provide this advantage.

The emitted laser beam is focused down to a millimeter or submillimeter sized spot with the use of the focusing lens 28. Consideration of laser safety issues suggests that a short focal length focusing lens be used to ensure that the energy fluence rate (W/cm$^2$) is low except at the focus of the lens where the tissue sample to be perforated is positioned. Consequently, the hazard of the laser beam is minimized.

Figure 4:
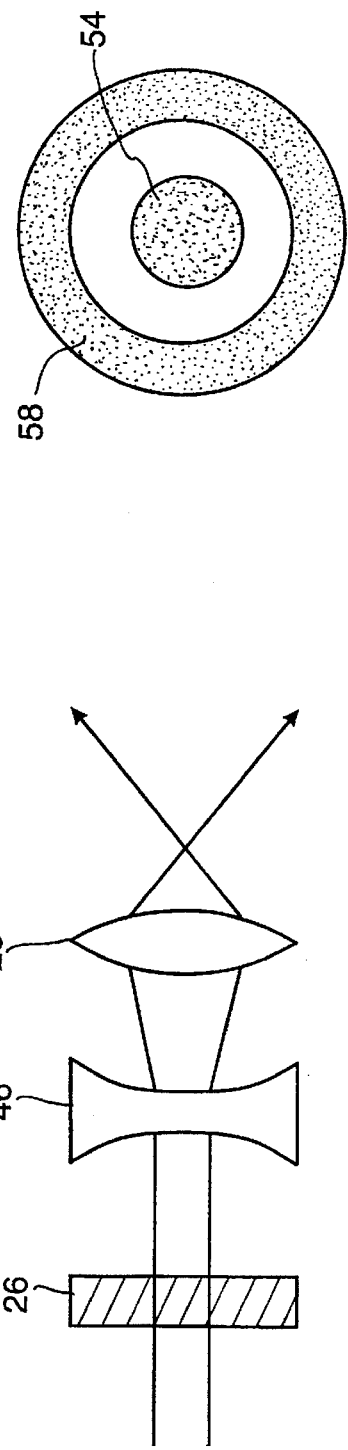
FIG. 4 shows an alternative focusing mechanism.

The beam can be focused so that it is narrower along one axis than the other in order to produce a slit-shaped perforation through the use of a cylindrical focusing lens 27. This lens, which focuses the beam along one axis, is placed in series with the transmitting focusing lens 28. When perforations are slit-shaped the pain associated with the perforation is considerably reduced Optionally, the beam can be broadened, for instance through the use of a concave diverging lens 46 (see FIG. 4), prior to focusing through the focusing lens 28. This broadening of the beam results in a laser beam with an even lower energy fluence rate a short distance beyond the focal point, consequently reducing the hazard level. Furthermore, this optical arrangement reduces the optical aberrations in the laser spot at the treatment position, consequently resulting in a more precise perforation.

Figure 5A:
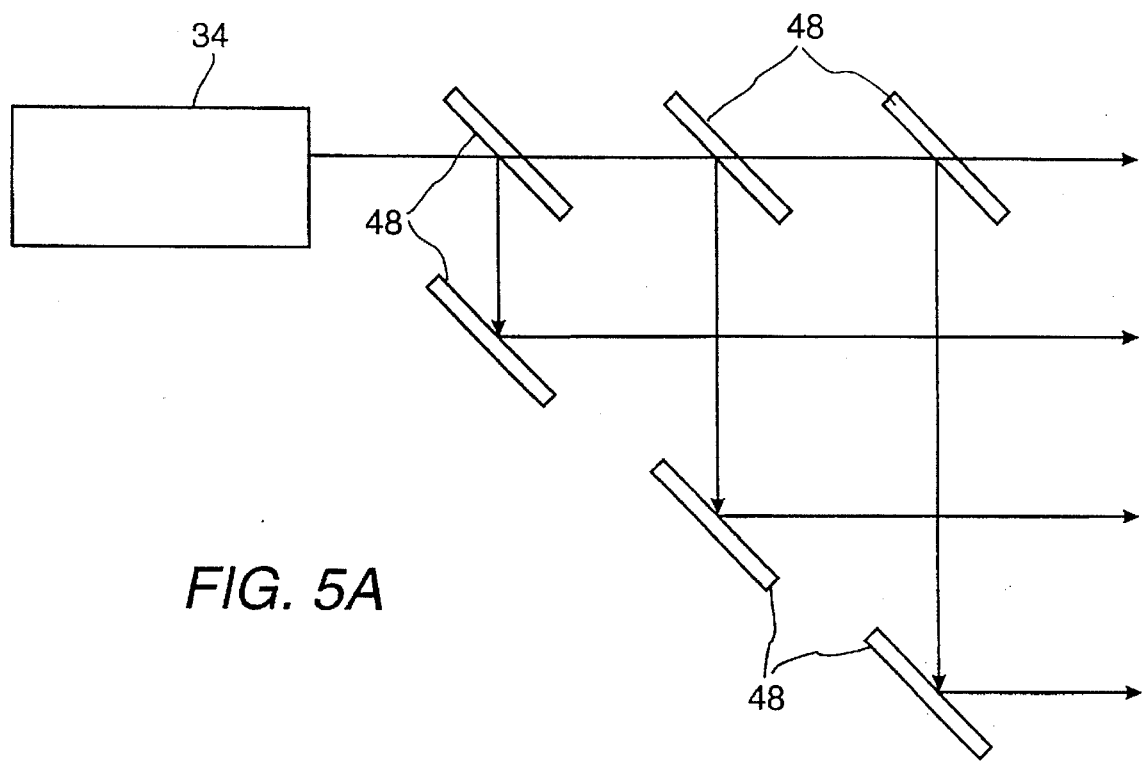
FIG. 5 shows optional beam splitters for creating multiple simultaneous perforations.
Figure 5B:
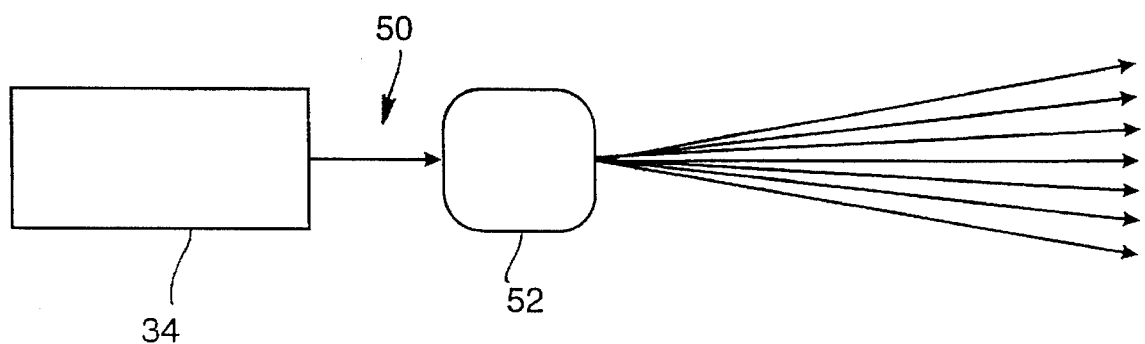

Also optionally, the beam can be split by means of a beam-splitter to create multiple beams capable of perforating at several sites simultaneously or near simultaneously. FIG. 5 provides two variations of useful beam splitters. In one version, multiple beam splitters 48 such as partially silvered mirrors, dichroic mirrors, or beam-splitting prisms can be provided after the beam is focused. Alternatively, an acousto-optic modulator 52 can be supplied with modulated high voltage to drive the modulator 52 and bend the beam. This modulator is outside the laser cavity. It functions by deflecting the laser beam sequentially and rapidly at a variety of angles to simulate the production of multiple beams.

A small heater, such as a thermoelectric heater 32, is optionally positioned at the end of the laser applicator proximal to the site of perforation. The heater raises the temperature of the skin and capillaries in the tissue to be perforated prior to laser irradiation. This increases blood flow, which increases the volume of blood collected when the device is used for that purpose. A suggested range for skin temperature is between 36° C. and 45° C., although any temperature which causes vasodilation and the resulting increase in blood flow without altering the blood chemistry is appropriate.

A container 68 is optionally fitted into the laser housing and is positioned proximal to the perforation site. The container reduces the intensity of the sound produced when the laser beam perforates the patient's tissue, increases the efficiency of blood collection, and collects the ablated tissue.

The container is shaped so as to allow easy insertion into the laser housing and to provide a friction fit within the laser housing. FIG. 8 shows the container inserted into the laser housing and placed over the perforation site.

The shape and size of the container are such as to allow insertion into the applicator, and to allow collection of the blood sample and/or ablated tissue. Preferably, the container is bullet-shaped, with a volume of around 1.5 milliliters.

In the preferred embodiment, the container is constructed of glass or plastic. In one embodiment, the container is evacuated. The optional vacuum in the container exerts a negative pressure over the perforation site, thereby increasing the efficiency in blood collection. The container is optionally coated with anticoagulating and/or preservative chemicals. Examples of preservatives include Ethylenediaminetetraacetic Acid (EDTA) or sodium benzoate. Examples of anticoagulating chemicals are sodium heparin and sodium citrate.

The container's end proximal to the perforation site is optionally sealed air-tight with a plug 70. The plug is constructed of material of suitable flexibility to conform to the contours of the perforation site (e.g., the finger). The desired perforation site is firmly pressed against the plug. The plug's material is impermeable to gas transfer. Furthermore, the plug's material is thin enough to permit perforation of the material as well as perforation of the skin by the laser. In the preferred embodiment, the plug is constructed of rubber.

Figure 9:
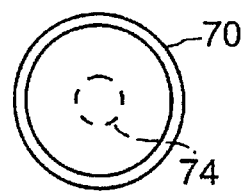
FIG. 9 shows a plug and plug perforation center.

The plug perforation center 74, as shown in FIG. 9, is preferably constructed of a thin rubber material. The thickness of the plug is such that the plug can maintain the vacuum prior to perforation, and the laser can perforate both the plug and the tissue adjacent to the plug. For use with an Er:YAG laser, the plug should be in the range of approximately 100 to 500 microns thick, but at the most 1 millimeter thick.

The plug perforation center 74 is large enough to cover the perforation site. Optionally, the perforated site is a round hole with an approximate diameter ranging from 0.1–1 mm, or slit shaped with an approximate width of 0.05–0.5 mm and an approximate length up to 2.5 mm. Thus, the plug perforation center is sufficiently large to cover perforation sites of these sizes.

The perforation site is firmly pressed against the rubber material. Optionally, an annular ring of adhesive can be placed on the rubber plug to provide an air-tight seal between the perforation site and the container. Preferably the perforation site on the plug is stretched when the tissue is pressed against the plug. This stretching of the plug material causes the hole created in the plug to expand beyond the size of the hole created in the tissue. As a result, the blood and/or serum can flow unimpeded into the container 68.

The container 68 includes a window 72 that is constructed of an infrared transmitting material and is positioned in the pathway of the laser beam, at the end of the container proximal to the beam. The laser beam penetrates the container through the window, perforates the plug perforation center 74, and perforates the patient's tissue. In the preferred embodiment, the infrared transmitting material is quartz, but other examples of suitable infrared materials include rock salt, germanium, and polyethylene.

Figure 10:
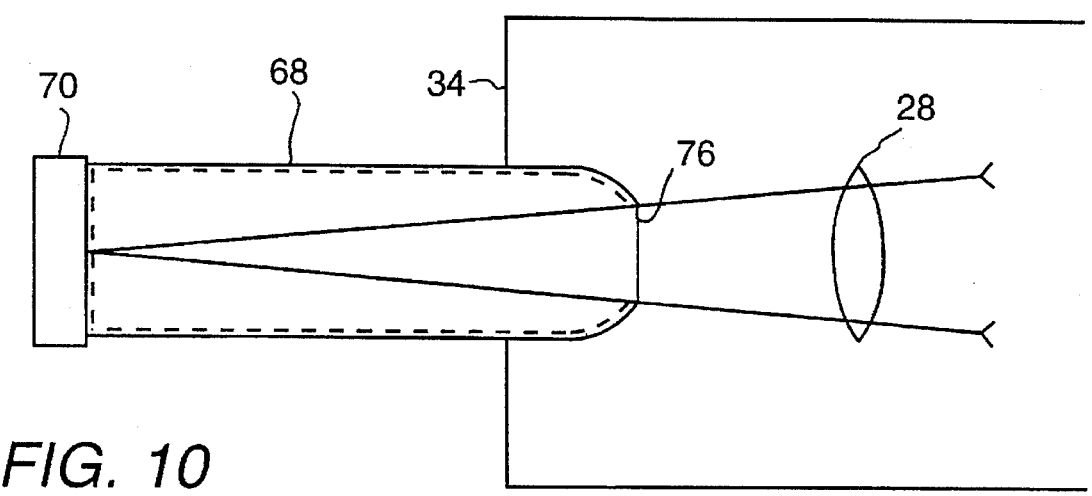
FIG. 10 shows an optional container for collecting ablated tissue and reducing noise resulting from the interaction between the laser and the patient's tissue.

In a second embodiment of the container, as shown in FIG. 10, the container 68 includes a hole 76 through which the laser passes. In this second embodiment, the container solely collects ablated tissue. As in the first embodiment, the perforation site is firmly pressed against the container. The container can optionally include a plug proximal to the perforation site, however it is not essential because there is no need to maintain a vacuum in the second embodiment. Both embodiments of the container reduce the noise created from interaction between the laser beam and the patient's tissue and thus alleviate the patient's anxiety and stress.

Optionally, the container is disposable, so that the container and plug can be discarded after use. Additionally, the container can contain reagents for various tests to be performed on the collected blood. Examples of such reagents are sodium heparin and other reagents known in the art to be used in standard blood chemistry tests. See, for example, Garza, D. et al., *Phlebotomy Handbook* (3d edition), Appleton and Lang Pub. Co., Norwalk, Conn., 1993, which is incorporated herein by reference. The reagents are positioned so that they will not be in the pathway of the laser light. The reagents are preferably present in a dry form, coating the interior walls of the container, and thus readily available for interaction with the blood sample as it is collected.

Figure 11:
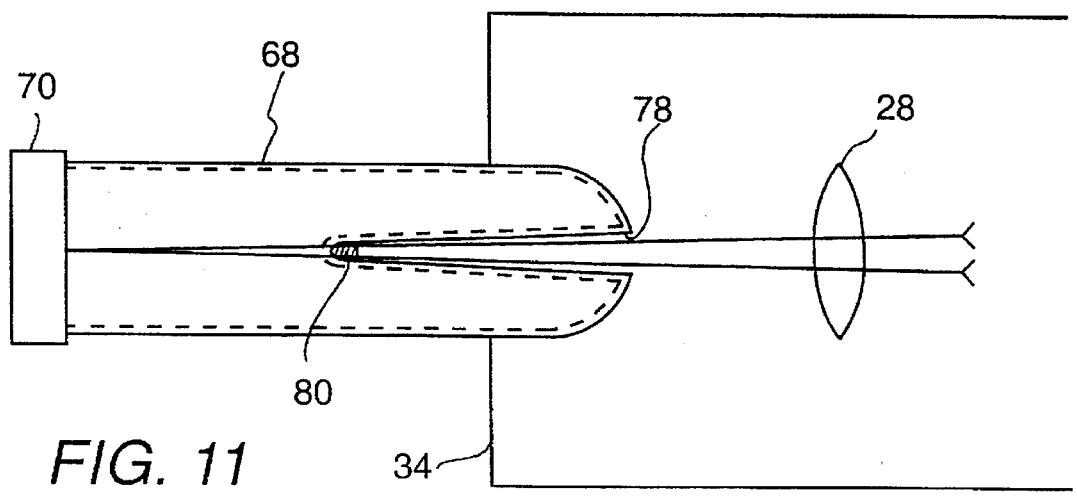
FIG. 11 shows an optional version of the collection container which is especially useful when the container includes a reagent for mixing with the sample.

A preferable configuration for the container when it contains a reagent is shown in FIG. 11. In this configuration, the container has an indentation 78 at the base such that any fluid reagent present in the container will not fall into the line of fire of the laser beam when the container is held either vertically or horizontally. The apex 80 of the indented area is made of a infrared-transparent substance such as quartz.

When reagents are present in the container prior to collection of the blood sample, it is beneficial to label the container in some manner as to the reagents contained inside, or as to the test to be performed on the sample using those reagents. A preferred method for such labelling is through the use of color-coded plugs. For example, a blue plug might indicate the presence of reagent A, while a red plug might indicate the presence of reagents B plus C within the container.

In order to sterilize the skin before perforation, a sterile alcohol-impregnated patch of paper or other thin material can optionally be placed over the site to be perforated. This material can also prevent the blowing off of potentially infected tissue in the plume released by the perforation. The material must be transparent to the laser beam. Examples of such material are a thin layer of quartz, mica, or sapphire. Alternatively, a thin layer of plastic, such as a film of polyvinyl chloride, can be placed over the skin. Although the laser beam will perforate the plastic, the plastic prevents most of the plume from flying out and thus decreases any potential risk of contamination from infected tissue. Additionally, a layer of a viscous sterile substance such as vaseline can be added to the transparent material or plastic film to increase adherence of the material or plastic to the skin and further decrease plume contamination. Additionally, such a patch can be used to deliver allergens, local anesthetics or other pharmaceuticals as described below.

Figure 6:
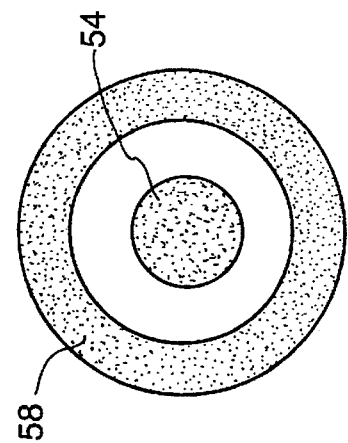
FIG. 6 shows a patch which can be used to sterilize the perforation site.

Examples of such a patch are provided in FIGS. 6 and 7. In FIG. 6, alcohol impregnated paper 54 is surrounded by a temporary adhesive strip 58. Side views of two alternative patches are shown in FIG. 7, where a sterilizing alcohol, antibiotic ointment, allergen, or pharmaceutical is present in the central region of the patch 60. This material is held in place by a paper or plastic layer 62, optionally with a laser-transparent material 64 such as mica, quartz or sapphire which is transparent to the laser beam at the center of the patch. The patch can be placed on the skin using an adhesive 66.

Factors which should be considered in defining the laser beam are wavelength, energy fluence, pulse temporal width and irradiation spot-size. The wavelength is determined by the laser material, such as Er:YAG, used in the device. The pulse temporal width is a consequence of the pulse width produced by the bank of capacitors, the flashlamp, and the laser rod material. The pulse width is optimally between 1 and 1,000 microseconds. The laser beam is focussed precisely on the skin, creating a beam diameter at the skin in the range of 0.1–1 mm, or optionally a slit-shaped beam ranging in width from 0.05 to 0.5 mm, and in length up to 2.5 mm. The energy density, which is a function of laser energy output (in Joules) and size of the beam at the focal point ($cm^2$), should be in the range of 10–100,000 $J/cm^2$. The focal length of the lens can be of any length, but in one embodiment of the device is 30 mm. The energy fluence rate is preferably in the range of $1.3 \times 10^4$ to $6.4 \times 10^{10}$ Watts/$cm^2$ and concurrently the energy fluence rate is preferably in the range of $1.3 \times 10^1$ to $6.4 \times 10^7$ Watts/$cm^2$.

The device operates as follows: The power interlock switch is initiated, thus starting the charging of the capacitors. The device is manipulated in such a way that a portion of the patient's skin is positioned at the site of the laser focus within the applicator. For blood collection, the location of the perforation is optimally at a site where the blood flow is high. Examples of such regions of the skin are on a fingertip, or the heel of a foot. For perforation for delivery of anesthetics or pharmaceuticals or for immunization, a region of the skin which has less contact with hard objects or with sources of contamination is preferred. Examples are skin on the arm, leg, abdomen or back. Optionally, the skin heating element is activated at this time.

Preferably a holder is provided with a hole coincident with the focal plane of the optical system. Optionally, a spring-loaded interlock 36 can be attached to the holder, so that when the patient applies a small amount of pressure to the interlock, to recess it to the focal point, a switch is closed and the laser will initiate a pulse of radiation. In this setup, the focal point of the beam is not in line with the end of the holder, until that end is depressed. In the extremely unlikely event of an accidental discharge of the laser before proper positioning of the tissue at the end of the laser applicator, the optical arrangement will result in an energy fluence rate that is significantly low, thus causing a negligible effect on unintentional targets.

For certain purposes, it is useful to create multiple perforations of the skin simultaneously or in rapid sequence. To accomplish this, a beam-splitter can optionally be added to the device.

Drawing Blood or Serum

The device can be used to perforate the skin to the capillary layer to allow the collection of blood. The blood can be used for a wide variety of tests, such as to determine blood chemistry (blood sugar, CBC, urea, electrolytes, creatinine, cholesterol, etc.), and/or it can be fractionated into its components, such as serum and cells, for a variety of purposes, such as determination of red blood cell count. The blood can also be used for such purposes as genetic analysis for genetic counseling.

With the other parameters set, the intensity of the laser pump source will determine the intensity of the laser pulse, which will in turn determine the depth of the resultant perforation. Therefore, various settings on the device can be provided to allow penetration of different thicknesses of skin.

As described above, the skin can be preheated to dilate the capillaries and increase the blood flow before perforation. This increased blood flow allows a greater volume of blood to be collected and obviates the need for multiple perforations. Preheating can be accomplished by the addition of a preheater, as described above, or by other means of preheating the skin prior to positioning it on the laser applicator part of the device.

Optionally, a beam-dump is positioned in such a way as not to impede the use of the laser for puncturing fingertips. The beam-dump will absorb any stray electromagnetic radiation from the beam which is not absorbed by the tissue, thus preventing any scattered rays from causing damage. The beam-dump is easily removable for situations when the presence of the beam-dump would impede the placement of a body part on the applicator.

This method of drawing blood creates a very small zone in which tissue is vaporized, and only an extremely small zone of thermal necrosis. A practical round hole can range from 0.1–1 mm in diameter, while a slit shaped hole can range from approximately 0.05–0.5 mm in width and up to approximately 2.5 mm in length. As a result, healing is quicker or as quick as the healing after a skin puncture with a sharp implement.

The blood can be collected into a suitable vessel, such as a small test tube or a capillary tube, or in a container placed between the laser and the tissue as described above. The laser of this invention is particularly suited to collection of blood because it does not coagulate the blood upon penetration of the skin. Furthermore, the process is non-contact and so neither the patient, the blood to be drawn, or the instrument creating the perforation is contaminated.

Delivery of Pharmaceuticals

By appropriate modification of the power level, and/or the spot size of the laser beam, perforations can be made which do not penetrate the skin as deeply as described above. These perforations can be made through only the outer surfaces, such as the keratin layer or both the keratin layer and the epidermis. Optionally an optical beam-splitter can be employed so that either single perforations or a number of perforations within a desired area can be made. After perforation, the pharmaceutical can be applied to the skin in a formulation such as a cream, lotion or patch.

Immunization

As for delivery of pharmaceuticals, antigens can be administered through the skin for immunization purposes. The perforations are made through the outer layers of the skin, either singly or multiply, and the immunogen is provided in an appropriate formulation. For booster immunizations, where delivery over a period of time increases the immune response, the immunogen can be provided in a formulation which penetrates slowly through the perforations, but at a rate faster than possible through unperforated skin.

Delivery of Anesthesia

Localized anesthetics can be delivered using the method and device of this invention. Topically applied anesthetics must penetrate the keratin layer in order to be effective. Presently, compounds acting as drug carriers are used to facilitate the transdermal diffusion of some drugs. These carriers sometimes alter the behavior of the drug, or are themselves toxic. The energy level on the device can be set appropriately to penetrate the keratin layer without penetrating to the capillary layer. Anesthetic can then be applied to the perforations, for example in a salve impregnated patch.

Delivery of Allergens

This device and method can also be applied to the delivery of allergens for example for allergy testing. Multiple perforations can be made, through the outer layer of the skin, but not penetrating to the capillary level. A variety of allergens can then be applied to the skin, as in a skin patch test.

The following examples are descriptions of the use of the device of this invention for the purpose of drawing blood. These examples are not meant to limit the scope of the invention, but are merely one embodiment.

EXAMPLE 1

An infrared laser radiation pulse was formed using a solid state, pulsed, multimode Er:YAG laser consisting of two flat resonator mirrors, an Er:YAG crystal as an active medium, a power supply, and a means of focusing the laser beam. The wavelength of the laser beam was 2.94 microns. The duration of the pulse was approximately 100 microseconds. The elliptical spot size was approximately 0.2–0.3 by 1–2 mm. Impulse energy used was 0.7, 0.9 or 2.0 J for thin to thick skin respectively. Single pulses were used, but in one test, 6 pulses per minute were used, each irradiating a separate piece of tissue.

The operating parameters were as follows: The energy per pulse was 2 Joules, with the size of the beam at the focal point being 0.2 mm, creating an energy fluence of $10^3$ J/cm$^2$. The pulse temporal width was 100 microseconds, creating an energy fluence rate of $1 \times 10^7$ Watts/cm$^2$.

Each patient's finger was treated prior to perforation with 96% ethyl alcohol to remove bacteria. The finger was placed at the focal point of the laser, and the laser was discharged. The blood was drawn from the perforation with a glass capillary tube. The volume of blood drawn (with no squeezing of the finger) ranged from 0.5–1.0 ml. This blood did not differ in chemistry from comparable samples obtained by lancet puncture during control tests. The pain elicited by laser perforation was estimated to be equal to or less than the pain elicited by the stabbing puncture of a lancet.

Morphological analysis of the effect of the laser perforation on the skin tissue showed minimal area of thermal destruction (less than 20–40 microns beyond the edge of the perforation produced) without any signs of carbonization. The wounds were cone shaped. The depth and width of the wounds were found to be proportional to the energy fluence and were approximately related to the inverse duration of the laser pulse.

EXAMPLE 2

The laser perforator comprises a flashlamp (PSC Lamps, Webster, N.Y.), an Er:YAG crystal (Union Carbide Crystal Products, Washagoul, Wash.), optical-resonator mirrors (CVI Laser Corp., Albuquerque, N.M.), an infrared transmitting lens (Esco Products Inc., Oak Ridge, N.J.), as well as numerous standard electrical components such as capacitors, resistors, inductors, transistors, diodes, silicon-controlled rectifiers, fuses and switches, which can be purchased from any electrical component supply firm, such as Newark Electronics, Little Rock, Ark.

EXAMPLE 3

An infrared laser radiation pulse was formed using a solid state, pulsed, multimode Er:YAG laser consisting of two flat resonator mirrors, an Er:YAG crystal as an active medium, a power supply, and a means of focusing the laser beam. The wavelength of the laser beam was 2.94 microns. The duration of the pulse was approximately 100 microseconds. The elliptical spot size was approximately 0.2–0.3 by 1–2 mm. Impulse energy used was 0.7, 0.9 or 2.0 J for thin to thick skin respectively. Single pulses were used, but in one test, 6 pulses per minute were used, each irradiating a separate piece of tissue.

The operating parameters were as follows: The energy per pulse was 2 Joules, with the size of the beam at the focal point being 0.2 mm by 1 mm, creating an energy fluence of $10^3$ J/cm$^2$. The pulse temporal width was 100 microseconds, creating an energy fluence rate of $1 \times 10^7$ Watts/cm$^2$.

Each patient's finger was treated prior to perforation with 96% ethyl alcohol to remove bacteria. The finger was placed at the focal point of the laser, and the laser was discharged. The blood was drawn from the perforation with a glass capillary tube. The volume of blood drawn (with no squeezing of the finger) ranged from 0.5–1.0 ml. This blood did not differ in chemistry from comparable samples obtained by lancet puncture during control tests. The pain elicited by laser perforation was estimated to be less than the pain elicited by the stabbing puncture of a lancet.

Morphological analysis of the effect of the laser perforation on the skin tissue showed minimal area of thermal destruction (less than 20–40 microns beyond the edge of the perforation produced) without any signs of carbonization. The wounds were slit shaped. The depth and width of the wounds were found to be proportional to the energy fluence and were approximately related to the inverse duration of the laser pulse.

EXAMPLE 4

Perforation is performed as in Example 1 or 3 except that the device is modified to include a blood collection tube, fitted tightly between the front end of the laser device and the focal point of the laser, through which the laser beam passes. The tube is 2.0 cm in length and 1.0 cm in diameter, with an indentation in the bottom which pushes the bottom 1.0 cm into the center of the tube. As a result, any fluid or crystallized additive such as the anticoagulant sodium heparin will not fall into the line of fire of the laser beam when the tube is held either vertically or horizontally. The apex of the indented area is made of a quartz disc which is transparent to the laser beam.

The distal end of the tube is covered by a rubber plug. The plug is coated on the outside with an adhesive to cause adherence of the plug to the skin to be perforated. The tube itself is maintained with an interior vacuum prior to perforation. The tube is further coated on the inside with sodium heparin to act as an anticoagulant for purposes of performing a blood count on the sample obtained.

The laser is then fired, causing the laser beam to pass through the tube, perforating only the distal end (the plug) of the tube as well as the skin. A specimen of blood of approximately 1 cc will then flow into the tube and mix with the sodium heparin. All of the blood specimen as well as any exploded/ablated tissue is thus contained within the tube, preventing contamination and the spread of disease.

While embodiments and applications of this invention have been shown and described, it would be apparent to those skilled in the art that many more modifications are possible without departing from the inventive concepts herein. The invention, therefore, is not to be restricted except in the spirit of the appended claims.

We claim:

1. A laser perforator device for perforating skin comprising
   a) a lasing element which emits a pulsed beam;
   b) a power source;
   c) a high voltage pulse-forming network linked to the power source;
   d) a means for exciting the lasing element, linked to the pulse-forming network;
   e) a laser cavity; and
   f) a focusing means which focuses the beam from said lasing element to at least one beam shaped as an ellipse at the focal point of the beam.

2. The device of claim 1 wherein the lasing element emits a wavelength that is strongly absorbed by tissue.

3. The device of claim 1 wherein the lasing element is selected from the group consisting of Er:YAG, pulsed $CO_2$, Ho:YAG, Er:YAP, Er/Cr:YSGG, Ho:YSGG, Er:GGSG, Er:YLF, Tm:YAG, Ho/Nd:YAlO$_3$, cobalt:MgF$_2$, HF chemical, DF chemical, carbon monoxide, deep UV lasers, diode lasers, and frequency tripled Nd:YAG.

4. The device of claim 1 wherein the laser wavelength is between 2 and 7 microns.

5. The device of claim 4 wherein the lasing element is an Er:YAG laser rod.

6. The device of claim 1 wherein the focusing means focuses the beam from said lasing element at a distance at least 10 mm from the lasing element.

7. The device of claim 1 further comprising an applicator positioned along the path of the beam between the laser cavity and the tissue to be perforated so that the focal point of the beam is within or at one end of the applicator.

8. The device of claim 7 wherein the applicator includes a beam dump.

9. The device of claim 7 wherein the applicator includes a fingertip access port.

10. The device of claim 7 further comprising an interlock between the high voltage pulse-forming network and the power source wherein the laser is not dischargeable unless the interlock is defeated.

11. The device of claim 10 wherein the interlock is a spring-loaded interlock which is activated by depressing the applicator.

12. The device of claim 11 wherein the applicator and spring are placed so that the applicator is positioned to defeat the interlock upon compression of the spring, and the focal point of the beam is located within about 5 mm of the distal end of the applicator when the interlock is defeated.

13. The device of claim 7 wherein the applicator is positioned so that the beam is completely enclosed at the time of perforation by the housing, the applicator and the tissue to be perforated.

14. The device of claim 7 further comprising a means for heating the applicator wherein the means for heating the applicator is adjacent to the applicator.

15. The device of claim 14 wherein the means for heating the applicator comprises a thermoelectric heater.

16. The device of claim 1 wherein the power source is a battery pack.

17. The device of claim 16 wherein the battery pack is a rechargeable battery pack.

18. The device of claim 1 wherein the means for exciting the lasing material is selected from a flashlamp and a diode laser.

19. The device of claim 18 wherein the diode laser is anterior to the lasing material, and the laser beam from the diode laser is focused on the lasing material through a collimating lens.

20. The device of claim 1 further comprising a container unit, positioned between the lasing element and the tissue, for the collection of biological or other matter released by perforation of the tissue, through which the laser beam passes and wherein the container is closed except at the end proximal to the tissue.

21. The device of claim 20 wherein the container collects bodily fluids.

22. The device of claim 20 wherein the container collects ablated tissue.

23. The device of claim 20 wherein the container comprises a vacuum.

24. The device of claim 20 wherein the container further comprises a plug that conforms to the contours of the perforation site and is proximal to the perforation site.

25. The device of claim 24 wherein the plug maintains a vacuum in the container.

26. The device of claim 24 wherein the plug is constructed of a material that is impermeable to gas transfer.

27. The device of claim 24 wherein the plug is constructed of rubber.

28. The device of claim 24 wherein the plug includes a plug perforation center.

29. The device of claim 28 wherein the plug perforation center is constructed of rubber with a thickness in the range of approximately 100 to 500 microns.

30. The device of claim 20 wherein the container includes an entry for the laser beam.

31. The device of claim 30 wherein the entry for the laser beam is a window positioned in the pathway of the laser beam, wherein the window is transparent to the laser beam.

32. The device of claim 31 wherein the window comprises an infrared transmitting material.

33. The device of claim 30 wherein the window is constructed of a material selected from the group consisting of quartz, rock salt, germanium, and polyethylene.

34. The device of claim 30 wherein the entry for the laser beam is a hole positioned in the pathway of the laser beam.

35. The device of claim 20 wherein the container is coated with an anticoagulating chemical.

36. The device of claim 35 wherein the anticoagulating chemical is selected from sodium heparin and sodium citrate.

37. The device of claim 20 wherein the container is coated with a preservative.

38. The device of claim 37 wherein the preservative is selected from Ethylenediaminetetraacetic Acid and sodium benzoate.

39. The device of claim 20 wherein the container unit comprises a main receptacle, comprising a) a rim against which the tissue is pressed;

b) a lens, at least partially transparent, through which the beam passes; and c) a wall extending from the perimeter of the lens to the rim, enclosing the region between the tissue and the lens.

40. The device of claim 39 wherein the container unit further comprises a base.

41. The device of claim 40 wherein the base further comprises a means for activating the laser perforator device.

42. The device of claim 41 wherein the base further comprises a means for disengaging a safety mechanism on the laser perforator device.

43. The device of claim 39 wherein the container unit further comprises a vessel for the collection of liquid and/or particulate matter released by the perforation of the tissue.

44. The device of claim 43 wherein the vessel has an open end and the vessel further comprises a stop to be placed into the open end to keep contaminants out of the vessel.

45. The device of claim 1 wherein the focusing means focuses the beam from said lasing element in an elliptical shape capable of creating a slit in a patient's tissue with a width between about 0.05 and about 0.5 mm and a length of equal to or less than about 2.5 mm.

46. The device of claim 45 wherein the width of the slit is about 0.2 mm and the length of the slit is about 1.0 mm.

47. The device of claim 1 wherein at the focal point one axis of the beam measures between about 0.05 and about 0.5 mm and the other axis of the beam measures less than or equal to about 2.5 mm.

48. A laser perforator device for perforating skin comprising a) a lasing element which emits a pulsed beam;

b) a power source;

c) a high voltage pulse-forming network linked to the power source;

d) a means for exciting the lasing element, linked to the pulse-forming network;

e) a laser cavity;

f) a beam splitter positioned to create multiple beams emanating from the device; and g) a focusing means which focuses each beam to an ellipse.

49. The device of claim 48 wherein the beam splitter is selected from a series of partially silvered mirrors, a series of dichroic mirrors, and a series of beam splitting prisms.

50. A laser perforator device for perforating skin comprising a) a lasing element which emits a pulsed beam;

b) a power source;

c) a high voltage pulse-forming network linked to the power source;

d) a means for exciting the lasing element, linked to the pulse-forming network;

e) a laser cavity;

f) a focusing means which focuses the beam from said lasing element to an ellipse; and an acousto-optic modulator outside the laser cavity wherein the modulator consecutively deflects the beam at different angles to create different sites of perforation on the skin.

* * * * *